(12) United States Patent
Cubizolles et al.

(10) Patent No.: US 11,442,055 B2
(45) Date of Patent: Sep. 13, 2022

(54) METHOD AND SYSTEM FOR DETECTING AN ANALYTE PRESENT IN A LIQUID SPECIMEN

(71) Applicant: Commissariat a l'Energie Atomique et aux Energies Alternatives, Paris (FR)

(72) Inventors: Myriam-Laure Cubizolles, Grenoble (FR); Thomas Bordy, Grenoble (FR); Frederic Revol-Cavalier, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 62 days.

(21) Appl. No.: 16/931,535

(22) Filed: Jul. 17, 2020

(65) Prior Publication Data
US 2021/0018488 A1 Jan. 21, 2021

(30) Foreign Application Priority Data
Jul. 17, 2019 (FR) ...................................... 19 08035

(51) Int. Cl.
*G01N 33/49* (2006.01)
*G01N 21/49* (2006.01)
(Continued)

(52) U.S. Cl.
CPC ...... *G01N 33/492* (2013.01); *B01L 3/502715* (2013.01); *G01N 1/08* (2013.01);
(Continued)

(58) Field of Classification Search
CPC .......... G01N 33/492; G01N 1/08; G01N 1/38; G01N 21/49; G01N 33/48785;
(Continued)

(56) References Cited

U.S. PATENT DOCUMENTS

| 5,863,801 A * | 1/1999 | Southgate .......... C12N 15/1013 436/63 |
| 2015/0152489 A1 | 6/2015 | Castro Signoret et al. |

(Continued)

OTHER PUBLICATIONS

French Preliminary Search Report dated Apr. 3, 2020 in French Application 19 08035 filed Jul. 17, 2019 (with English Translation of Categories of Cited Documents and Written Opinion), 12 pages.
(Continued)

*Primary Examiner* — Samuel P Siefke
*Assistant Examiner* — Henry H Nguyen
(74) *Attorney, Agent, or Firm* — Oblon, McClelland, Maier & Neustadt, L.L.P.

(57) ABSTRACT

The invention relates to a method for detecting an analyte present in a liquid specimen, including: injecting the liquid specimen into a detection chamber, the detection chamber having a non-zero volume enclosing polymeric beads covered with a reagent suitable for the analyte to be detected; capturing at least one image of at least one region of the detection chamber using a sensor; processing the image acquired by the sensor, which includes determining a texture level of the acquired image; and determining a concentration of the analyte depending on the texture level determined for the image.

9 Claims, 7 Drawing Sheets

(51) Int. Cl.
| | |
|---|---|
| *G01N 33/487* | (2006.01) |
| *B01L 3/00* | (2006.01) |
| *G01N 33/543* | (2006.01) |
| *G01N 33/53* | (2006.01) |
| *G01N 33/72* | (2006.01) |
| *G01N 1/08* | (2006.01) |
| *G01N 1/38* | (2006.01) |
| *G01N 1/28* | (2006.01) |
| *G01N 33/574* | (2006.01) |

(52) U.S. Cl.
CPC ............... *G01N 1/38* (2013.01); *G01N 21/49* (2013.01); *G01N 33/48785* (2013.01); *G01N 33/5304* (2013.01); *G01N 33/54313* (2013.01); *G01N 33/57419* (2013.01); *G01N 33/726* (2013.01); *B01L 2200/027* (2013.01); *B01L 2300/044* (2013.01); *B01L 2300/0672* (2013.01); *B01L 2300/0681* (2013.01); *B01L 2300/0816* (2013.01); *B01L 2300/0867* (2013.01); *G01N 33/721* (2013.01); *G01N 2001/288* (2013.01); *G01N 2001/2873* (2013.01)

(58) Field of Classification Search
CPC ......... G01N 33/5304; G01N 33/54313; G01N 33/57419; G01N 33/726; G01N 33/721; G01N 2001/2873; G01N 2001/288; B01L 3/502715; B01L 2200/027; B01L 2300/044; B01L 2300/0672; B01L 2300/0681; B01L 2300/0816; B01L 2300/0867; B01L 2400/049
See application file for complete search history.

(56) References Cited

U.S. PATENT DOCUMENTS

2016/0367986 A1* 12/2016 Tatnell ................... G01N 1/286
2018/0238775 A1* 8/2018 Kambara ................. G01N 1/08
2019/0079063 A1* 3/2019 Gilboa-Geffen ... G01N 33/5308

OTHER PUBLICATIONS

Park, T. S. et al., "Smartphone Detection of *Escherichia coli* From Field Water Samples on Paper Microfluidics," IEEE Sensors Journal, vol. 15, No. 3, Mar. 2015, XP011570933, 6 pages.

Cui, W. et al., "Cellphone-Enabled Microwell-Based Microbead Aggregation Assay for Portable Biomarker Detection," ACS Sensors, vol. 3, No. 2, Feb. 23, 2018, XP055680783, 9 pages.

Wu, Y. et al., "Deep learning enables high-throughput analysis of particle-aggregation-based bio-sensors imaged using holography," arxiv.org, Cornell University Library, Oct. 24, 2018, XP081069575, 15 pages.

Mudanyali, O. et al., "Integrated rapid-diagnostic-test reader platform on a cellphone," Lab on a Chip, vol. 12, No. 15, Jan. 1, 2012, XP055058669, 9 pages.

Moon, S. et al., "Integrating microfluidics and lensless imaging for point-of-care testing," Biosensors and Bioelectronics, vol. 24, No. 11, Jul. 15, 2009, XP026150128, 7 pages.

Lee, S. A. et al., "A smartphone-based chip-scale microscope using ambient illumination," Lab on a Chip, vol. 14, No. 16, Jan. 1, 2014, XP055680660, 8 pages.

* cited by examiner

METHOD AND SYSTEM FOR DETECTING AN ANALYTE PRESENT IN A LIQUID SPECIMEN

TECHNICAL FIELD OF THE INVENTION

The present invention relates to a method and system for detecting an analyte present in a liquid specimen.

The system is notably suitable for detecting the presence of human haemoglobin in a stool sample, with a view to screening for colorectal cancer.

The system is also suitable for detecting analyte in samples such as:
- mud, for research into bacteria or fungi,
- earth, for research into pollutants or particular compounds (sulfates, iron, copper, etc.),
- plants (for example mushrooms, salads, vegetables, seeds, fruits, etc.) with a view to monitoring contamination (presence of pesticides, bacteria, etc.),
- animals, for example in the case of a biopsy of the ear tissue of livestock.

Mention may notably be made of the detection of the presence of mycotoxins in seeds, or the detection of pesticides in a particular environment (mud for example).

Prior Art

In the field of the prevention of colorectal cancer, haemoglobin is assayed in the laboratory after a sample of material has been taken.

The sampling devices may comprise a tool such as a swab, a strip or a spatula, inter alia. These tools are handled directly by the user of the test, who is required to take his own samples, and allow a unitary sample that is calibrated by the form of the tool to be taken. One known and used sampling solution consists in employing a cannula. The cannula is then inserted into a vial equipped with a septum system that limits the excess of material, thus allowing the specimen to be better calibrated. Another known solution consists in employing a container into which the faeces are placed, a sample then being taken by scraping using a cannula. In the field of taking soil samples, systems also exist that allow a calibrated core sample to be taken using a soil sampler. These known devices consist of a hollow rod that fills as it is pushed into the ground.

As regards the analysis, faecal haemoglobin is assayed with a dedicated piece of laboratory equipment that allows the immuno-agglutination of latex beads grafted with antibodies directed against human haemoglobin to be measured optically by turbidimetry. The major drawback of this solution is that the analysis can be performed only several days after the sample is taken. This implies a possible adverse alteration of the haemoglobin during transportation, and therefore requires a haemoglobin-stabilizing solution to be used.

Portable systems for measuring the aggregation of microbeads with a view to assaying biomarkers do exist. One is described in the publication "Cui, W, He, M., Mu, L., Lin, Z., Wang, Y., Pang, W., Reed, M. A., and Duan, X. *Cellphone-Enabled Microwell-based Microbead Aggregation Assay for Portable Biomarker Detection. ACS Sens.* 2018, 3, 2, 432-440". This study demonstrates quantitative assaying of prostate specific antigen (PSA) with microbeads covered with anti-PSA antibodies that aggregate in the presence of PSA. The portable system used consists in trapping these aggregated microbeads within wells contained in a microfluidic chip and optically measuring, using a smartphone interfaced with a portable optical microscope, the number of aggregated beads contained in the wells. The major drawback of this solution resides in the preparation of the specimen, which must be carried out manually outside of the system.

Other studies also describe direct use of smartphones and ambient light to detect micro-objects, such as beads or animal cells. This is the case in the publication "Lee, S. A.; Yang, C. *A Smartphone-Based Chip-Scale Microscope Using Ambient Illumination. Lab. Chip* 2014, 14 (16), 3056-3063".

The aim of the invention is to provide a solution allowing quantitative or semi-quantitative assaying of an analyte to be carried out in a way that is:
- simple,
- direct and rapid, i.e. on-site, without sample transfer to a laboratory and without employing hardware of excessive bulk, and
- reliable.

SUMMARY OF THE INVENTION

This aim is achieved via a method for detecting an analyte present in a liquid specimen, characterized in that it comprises steps of:
- positioning a medium including a detection chamber on a device for preparing by coring,
- preparing by coring a solid specimen and dissolving or re-suspending said solid specimen with a view to obtaining a liquid specimen,
- injecting said liquid specimen into said detection chamber, said detection chamber having a non-zero volume enclosing polymeric beads covered with a reagent suitable for said analyte to be detected, allowing an agglutination reaction in the presence of the analyte,
- capturing at least one image of at least one region of the detection chamber using a sensor,
- processing said image acquired by the sensor, this comprising determining a texture level of said acquired image, said texture level depending on the agglutination level of the polymeric beads in the presence of the analyte, and determining a concentration of said analyte depending on the texture level determined for said image.

According to one particularity, the capturing step is carried out by defocused imaging.

The invention also relates to a system for detecting an analyte present in a liquid specimen, comprising:
- a medium equipped with a fluidic circuit, said fluidic circuit comprising at least one injection channel and a detection chamber into which said injection channel opens, said detection chamber having a non-zero volume enclosing polymeric beads covered with a reagent suitable for said analyte to be detected,
- an optical read-out device, comprising an image sensor arranged to acquire an image of at least one region of the detection chamber,
- a processing unit configured to process each image acquired by the sensor, comprising a module for determining a texture level of each acquired image and a module for determining a concentration of said analyte depending on the texture level determined for each image, said texture level depending on the agglutination level of the polymeric beads in the detection chamber in the presence of the analyte.

According to one particularity, the sensor and the region of the detection chamber are positioned in a defocused manner.

According to another particularity, the optical read-out device comprises a source of light radiation arranged to emit light radiation through the detection chamber, said sensor being positioned on the other side of said source with respect to the region of the detection chamber.

According to another particularity, the medium consists of a micro-fluidic card made from a transparent or semi-transparent material.

According to another particularity, the system comprises a device for preparing the liquid specimen to be analysed, on which is fitted said medium, said preparing device comprising an implement for coring a sample of material and an implement for dissolving or re-suspending each core produced by said coring implement, to which is connected said injection channel of the fluidic circuit.

According to another particularity, the dissolving or re-suspending implement comprises one or more cuvettes each intended to receive a dissolving or re-suspending liquid.

According to another particularity, the preparing device comprises a body and the coring implement comprises one or more die-cutters that are movable with respect to the body, each die-cutter interacting translationally with said body in a main direction, between at least one rest state in which the die-cutter is plumb with a deposition surface intended to receive said sample of material and an actuated state in which the die-cutter is located inside a separate cuvette of the dissolution or re-suspension implement.

According to another particularity, each cuvette comprises an aperture and the system comprises at least one perforable film covering the aperture of each cuvette.

According to another particularity, the fluidic circuit comprises a region for filtering particles present in the liquid specimen.

According to another particularity, the optical read-out device and the processing unit are grouped together in one and the same device of smartphone type.

BRIEF DESCRIPTION OF THE FIGURES

Other features and advantages will become apparent from the following detailed description, which is given with reference to the appended drawings, in which.

DETAILED DESCRIPTION OF AT LEAST ONE EMBODIMENT

In the appended figures, a main axis (A) extending in a vertical direction, perpendicular to the surface on which the system of the invention is placed is defined, which axis will be referred to in the following description. The aforementioned surface may notably be the ground or any other planar medium.

The terms "upper", "lower", "above", "below" and equivalents used below in the description are to be understood with reference to said main axis (A).

The invention aims to allow an analyte to be assayed using the concept of agglutination of (nanoscale or micron-sized) polymeric (for example latex) beads. The invention may be used in any field, to take various types of sample, provided that the sample may be re-suspended or dissolved in a liquid medium.

The invention is applicable to any field in which it is possible to carry out a quantitative or semi-quantitative assay of a target of interest using the agglutination of micro- or nano-beads. These beads, which are micron-sized or most often nanoscale beads, are covered with a suitable reagent (antibodies for example) that recognises the target. In the presence of the latter, bridges form between the various beads: this is an agglutination reaction, for example immuno-agglutination. The larger the amount of target, the greater the aggregation of the beads with one another. It will be seen that an optical measurement of the scatter of light then allows the concentration of the target in the analysed specimen to be accurately quantified.

The invention is notably suitable for detecting the presence of human haemoglobin in faeces with a view to improving tests for screening for colorectal cancer.

As indicated above, mention may also be made of detecting the presence of mycotoxins in seeds or the presence of pesticides in a particular environment (mud for example).

The system of the invention comprises, inter a/ia, an integrated optical detection architecture and an integrated processing unit allowing it to be employed directly in the field.

Figure 1:
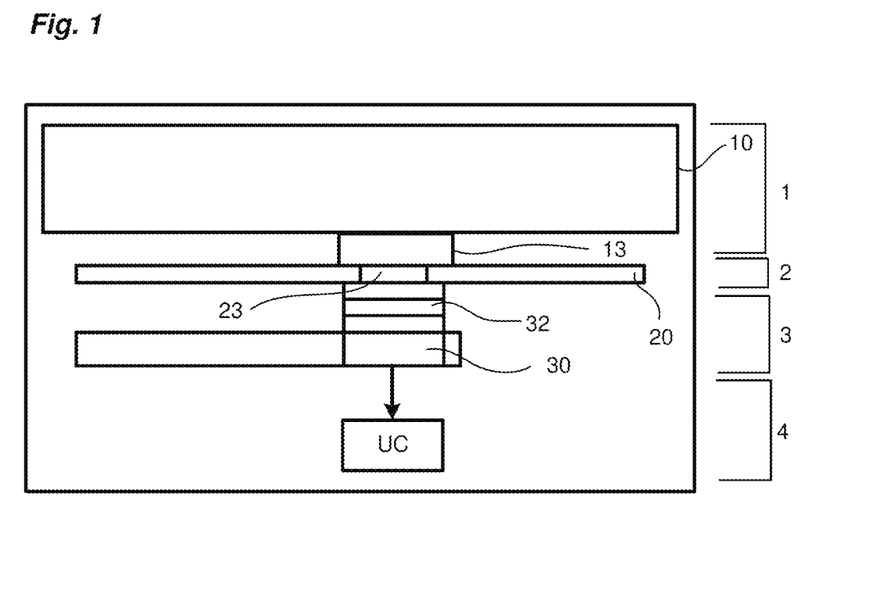
FIG. 1 schematically shows the system of the invention.

With reference to FIG. 1, the system of the invention advantageously has an architecture that is made up of a number of portions:
- a first portion 1 composed of a device for preparing a calibrated specimen from a sample of material;
- a second portion 2 composed of a micro-fluidic card equipped with a detection chamber in which the beads described above are placed in order to achieve the agglutination reaction;
- a third portion 3 composed of an optical read-out device notably comprising a sensor for capturing images of the detection chamber;
- a fourth portion 4 composed of a processing unit configured to process the images acquired by the sensor.

The system advantageously has an integral architecture, comprising a body, which is for example made of plastic, to which various elements required for the system to operate may be connected.

The first portion 1 of the system, which portion is formed of a device for preparing the specimen, may have various configurations. This preparing device plays a dual role: producing at least one calibrated specimen from a sample of material and ensuring a dissolution or re-suspension of this calibrated specimen in a liquid with a view to transfer to the micro-fluidic card equipped with the detection chamber.

It will be understood that the system of the invention is not limited to the preparing device described below and that it is able to work with a preparing device having different features. The system requires a solution for obtaining at least one calibrated specimen and for dissolving or re-suspending it in a liquid so as to be able to inject it into the micro-fluidic card for analysis.

Advantageously, the employed preparing device may allow a plurality of calibrated specimens to be prepared simultaneously from the same sample P of (advantageously soft) material. Non-limitingly, the device will possibly allow one to ten calibrated specimens to be prepared from the same sample. In the appended figures, the schematic representation of the device shows the simultaneous preparation of two separate specimens from the same sample P of material.

By way of example, the material will possibly be faeces of a living (notably human) being, mud, or a material present in the ground. However, the sample P will possibly also be of plant type (seeds of different sizes) or animal origin.

In the case of human faeces, the generated specimens will notably serve to detect the presence of haemoglobin with a view to screening for colorectal cancer.

Non-limitingly, the material of the sample P that serves as precursor for the preparation of the specimens must be soft enough to be cored using the user's strength alone. Regarding faeces, the hardness of the sample will possibly be comprised between 1 and 7 on the Bristol scale. However, with certain harder samples (such as for example hard seeds), it is possible to use the device solely to calibrate a specimen (without cutting/coring the sample), notably in the case where the size of the sample is smaller than the size of the die-cutter that is employed in the device.

The preparing device may take the form of an integral assembly that is easily transportable.

Figure 2A:
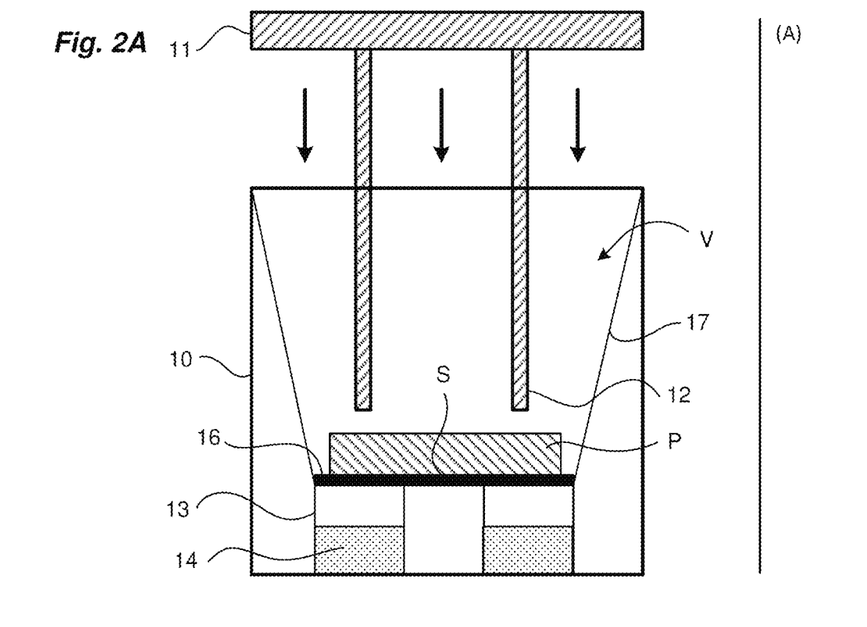
FIGS. 2A to 2C schematically show a first configuration of a preparing device able to be employed in the system of the invention, in three different operating states.
Figure 2B:
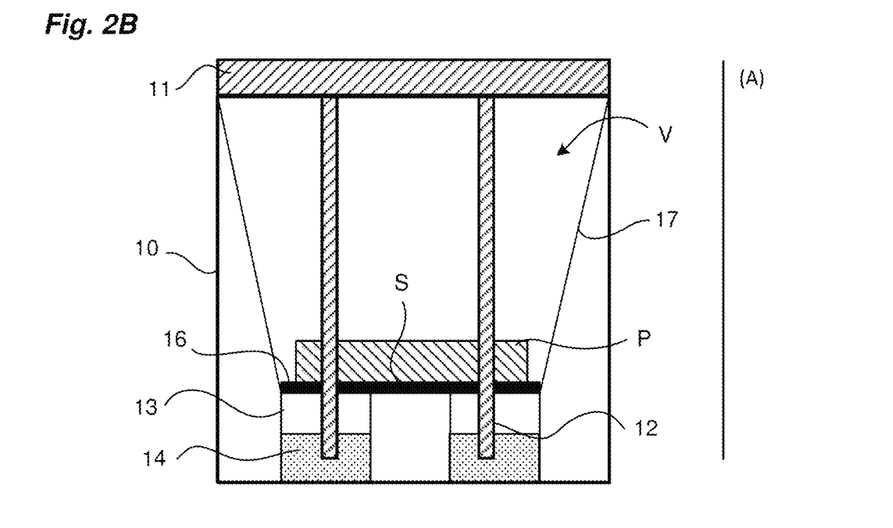
Figure 2C:
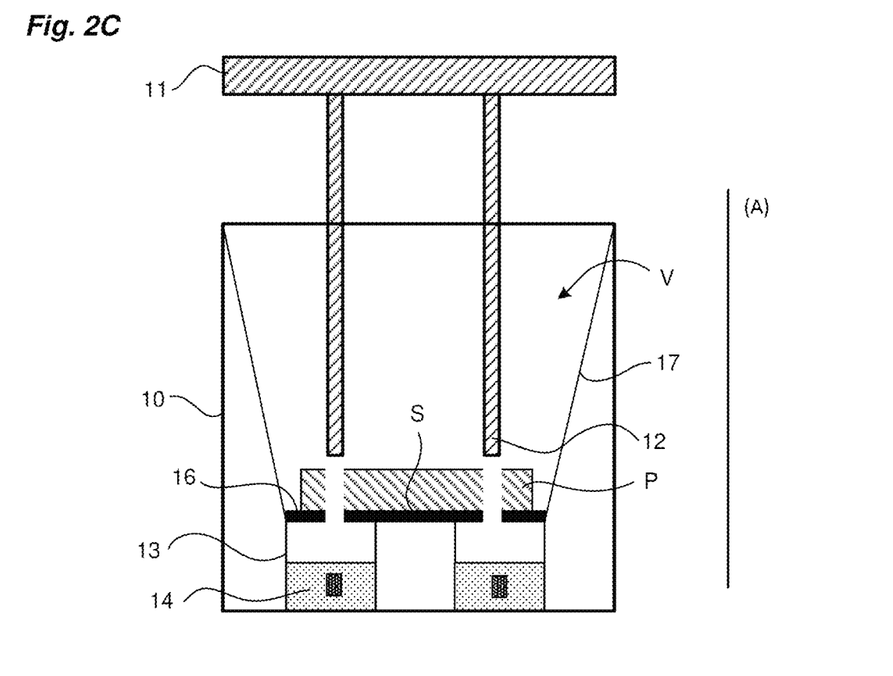
Figure 3:
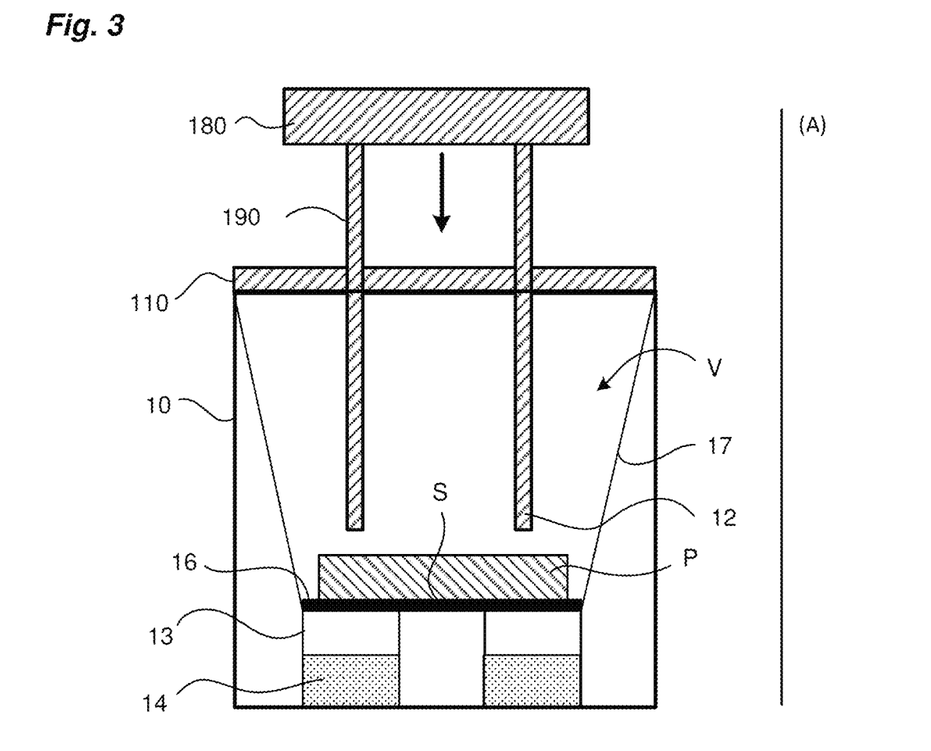
FIG. 3 schematically shows a second configuration of a preparing device able to be employed in the system of the invention, in the rest state.

FIGS. 2A to 2C show a first configuration of the preparing device, and FIG. 3 shows a second configuration of the preparing device.

In these two configurations, the preparing device may comprise a body defining an internal space V formed by assembling a container 10 and a cover 11, 110 that may be positioned on the container so as to close it. The container is advantageously intended to be placed on the ground or on any suitable medium. When the cover 11, 110 is placed on the container, the internal space V is advantageously isolated from the exterior hermetically.

Non-limitingly, the container 10 may be of cylindrical shape and have a bottom, one or more side walls and an upper aperture intended to be closed by the cover. Of course, any other shape could be suitable.

The device may comprise a medium taking the form of a platform housed in the internal space V of the container. The platform comprises a deposition surface S for receiving the sample from which one or more specimens will be prepared. This deposition surface S is advantageously planar and oriented perpendicular to the main axis (A).

The platform comprises a perforable film 16 the upper surface of which forms the deposition surface S for receiving the sample. Non-limitingly, the film may take the form of a plastic, polymer, elastomer (for example foam) or metal film that hermetically covers one or more cuvettes 13 located under the platform. It may also take the form of a multilayer element employing a plurality of the aforementioned materials. The perforation is achieved by simply pressing against the surface of the film in a direction transverse to said surface S and preferably normal to said surface. This perforation direction is therefore advantageously parallel to the main axis (A) defined above. It will be seen below that the pressure allowing the film 16 to be perforated is generated using at least one die-cutter 12 of the device.

The cuvettes form an implement for dissolving or re-suspending the specimens. Specifically, each cuvette 13 is intended to receive a liquid 14 chosen to allow the dissolution or re-suspension of the prepared specimen. One separate cuvette 13 is advantageously dedicated to each particular specimen prepared from the sample. There may be any number of cuvettes. There may possibly be between one and ten cuvettes. The number of cuvettes may be equal to the number of samples to be prepared, or may even be higher than the number of samples to be prepared. In the latter case, the additional cuvettes will possibly be used for calibration or control purposes or for example to preserve a reference so as to allow the aging over time of the solutions contained in the cuvettes to be monitored.

The preparing device of the invention comprises a coring implement intended to create one or more specimens from the sample P of material deposited on the deposition surface S of the platform.

For each calibrated specimen to be prepared, the coring implement comprises one separate die-cutter 12 intended to cut through the sample P of material in order to produce one calibrated specimen.

Advantageously, the coring implement comprises a plurality of die-cutters 12 in parallel, allowing a plurality of specimens to be produced simultaneously from the same sample P.

The coring implement is arranged so as to allow the die-cutters 12 to be translated in a given direction, normal to the deposition surface S and therefore parallel to the main axis (A).

Each die-cutter 12 may take the form of a hollow portion at the free end of a tube, the hollow portion of the tube defining the volume of the core created during the preparation of the specimen and therefore the volume of the die-cutter. The tubes are placed parallel to one another and are arranged so that their axis is parallel to the main axis (A). Each tube has one end fastened to a movable portion of the device (cover or movable assembly) and its free end, which comprises the hollow portion forming the die-cutter. Of course, any other form of die-cutter could be suitable, provided that the die-cutter allows the sample to be cored.

Particularly, in the first configuration shown in FIGS. 2A to 2C, the die-cutters 12 are borne directly by the cover 11 of the device. They are then oriented toward the interior of the container 10 when the cover 11 is placed on the container 10 to close it. A slide mechanism may be provided between the container 10 and the cover 11 in order to guide how the cover 11 is positioned on the container 10 in the direction of the main axis (A). As the cover is moved with the translational movement to be placed on the container, each die-cutter 12 cuts through one portion of the sample.

In the second configuration, which is shown in FIG. 3, the coring implement may comprise a movable mechanism that interacts with the body of the device by sliding. Non-limitingly, this movable mechanism may comprise a grippable member 180 located outside the body of the device, thus making it accessible to manual gripping. This grippable member 180 may take the form of a handle. The movable mechanism comprises an assembly that is translationally movable in the internal space V of the body of the device. Said grippable member 180 is connected to this movable assembly via at least one linking rod 190. Said linking rod is arranged to pass through the body of the device, through at least one aperture, thus forming a slide mechanism between the movable mechanism and the body of the device. The linking rod 190 allows the translational movement applied to the grippable member to be transmitted to the movable assembly. The link may pass through the cover 110 of the device, which is then fastened in place and forms part of the body of the device. As mentioned above, the movable assembly then comprises one or more die-cutters 12 each intended to cut through one portion of the sample P placed on the deposition surface S.

In these two configurations, two distinct states of the preparing device may be distinguished between:

A rest state in which the die-cutters 12 have their free end located plumb with the sample P placed on the deposition surface S. In other words, in this rest state, the free end of each die-cutter 12 is located above the sample. In the aforementioned first configuration, the cover 11 is therefore not on the container, closing it. In the second configuration, the movable assembly is raised and the grippable member 180 juts out with respect to the cover 110.

An actuated state in which the free end of each die-cutter 12 is housed in a corresponding cuvette 13. In the first configuration, the cover 11 then closes the container. In the second configuration, the movable assembly will have been translated downward along the main axis (A) by pressing on the grippable member 180.

Between its two states, each die-cutter 12 is firstly made to pass through the sample P in order to cut through it and then to perforate the film 16 covering one or more cuvettes. If the sample P cannot be cut through (because it is too small for example in the case of a seed), the die-cutter 12 allows the sample to be calibrated.

As already described, each cuvette 13 is intended to be filled with a liquid, those cuvettes that are located facing a die-cutter allowing specimens to be dissolved or re-suspended.

The second portion 2 of the system for its part comprises a single micro-fluidic card 20 intended to receive the liquid in which each calibrated specimen has been dissolved or re-suspended.

Figure 4:
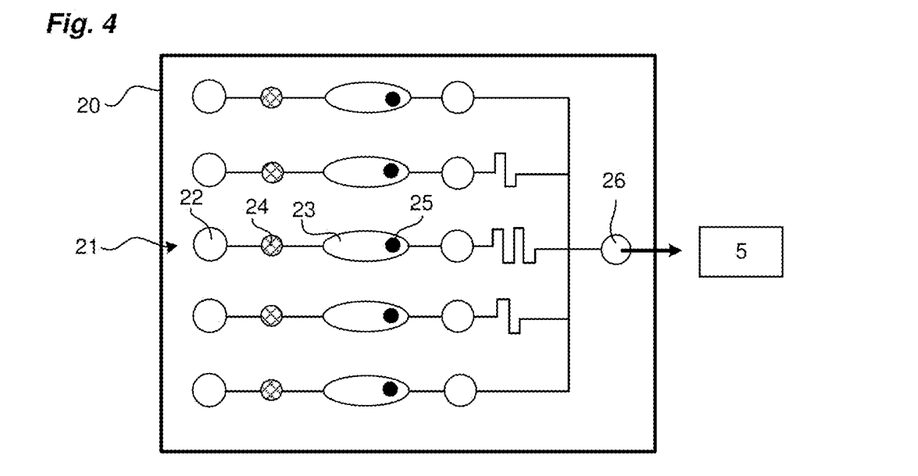
FIG. 4 schematically shows, seen from above, the micro-fluidic card able to be employed in the system of the invention.

As shown in FIG. 4, in the conventional way the micro-fluidic card 20 may take the form of a planar medium formed from a plurality of superposed layers that are adhesively bonded to one another. The card 20 comprises one or more fluidic circuits 21, each forming one separate fluidic analysis channel. A fluidic circuit 21 may be formed by a recess formed (for example by etching, moulding or machining) in one face of a layer of the card 20 and covered with another layer of the card.

Non-limitingly, the card 20 may comprise at least as many fluidic circuits 21 as there are cuvettes in the preparing device. In FIG. 4, by way of example, the card 20 comprises five identical fluidic circuits in parallel. The card 20 may also comprise one or more fluidic circuits that are termed reference fluidic circuits. These reference fluidic circuits may notably replace the cuvettes referred to as reference cuvettes above and which were employed to monitor the aging of the contained solutions.

The body of the system may comprise a housing into which the micro-fluidic card 20 may be inserted. The micro-fluidic card 20 thus takes the form of a cartridge that, with respect to the rest of the system, is removable and disposable. The insertion of the card 20 into the housing allows a seal-tight fluidic connection to be formed between a fluidic outlet connected to each cuvette 13 of the preparing device and a separate fluidic inlet 22 of each fluidic circuit produced in the card 20.

In the micro-fluidic card, each fluidic inlet is connected by an inlet channel to a detection chamber 23 formed from a cavity of non-zero volume, the shape of which is flared with respect to the cross section of the inlet channel.

Figure 5A:
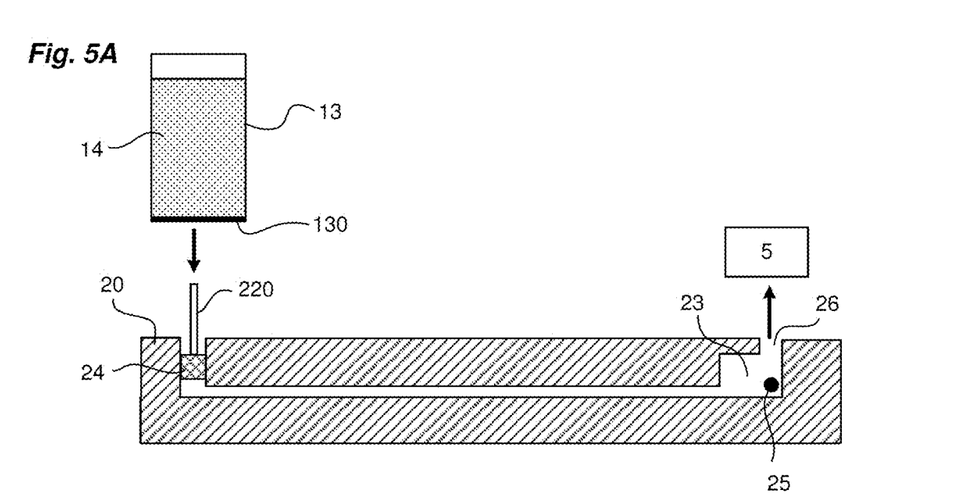
FIGS. 5A and 5B illustrate a concept of fluidic connection of the micro-fluidic card.
Figure 5B:
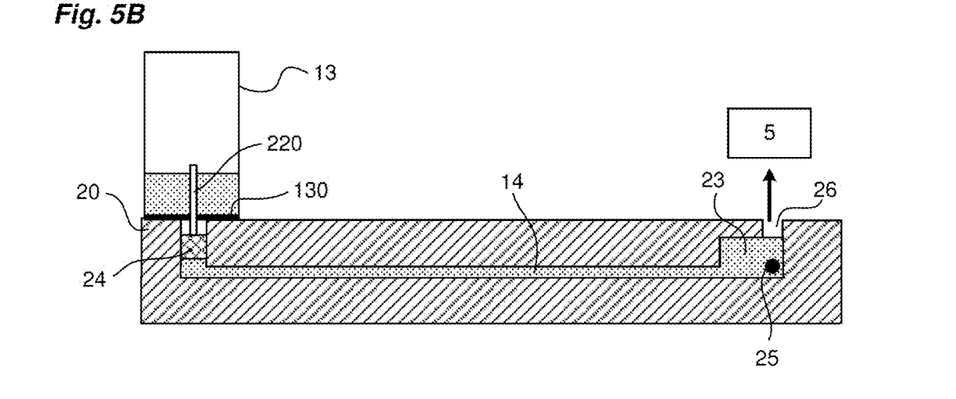

As shown in FIGS. 5A and 5B, non-limitingly, each fluidic inlet may be formed from a channel produced in a hollow needle 220 intended to interface with a cuvette 13 of the preparing device. The cuvette of the sampling system, which contains the liquid allowing the specimen to be re-suspended, may comprise, at its base, a septum 130 or a film that is perforable by the needle 220, for example at the moment of insertion of the micro-fluidic card 20 into its housing. As a variant, the fluidic connection may be ensured by an end-fitting that is connected to the cuvette via a valve equipped with a seal (an O-ring for example) allowing seal-tightness to be ensured. Any other solution may of course be envisaged.

Each fluidic circuit 21 may then be filled by gravity, or by employing a source of negative pressure as described below.

Between its inlet and its detection chamber, each fluidic circuit 21 may comprise a filtration region 24 intended to filter particles that will hinder the rest of the optical analysis. It may for example be a question of faecal particle debris in the case of stool samples, or even of blood cells (red blood cells and white blood cells) in the case of a blood sample. By way of example, the filtration region 24 may be composed of a reservoir, containing the one or more materials allowing the filtration to occur. It may for example be a question of cellulose, of expanded polyurethane or even of a polymer. The materials may be combined together to form a layer, beads or a slope if necessary.

Downstream of its filtration region, the fluidic circuit comprises its detection chamber 23. This detection chamber 23 is intended to contain the nano-beads 25, which are covered with a suitable reagent (antibodies for example) and necessary to detect the target of interest. These beads 25 are placed, in dried or freeze-dried form, in the chamber 23 and are kept within the chamber, for example using a mesh (a hydrophobic grid or filter) having a suitable size of mesh cell. It will be noted that the detection chamber 23 is dimensioned so that the (CMOS) sensor of the read-out device can acquire images. In particular, the thickness of the chamber, and the material(s) from which it is composed, are important criteria that must be taken into account.

The micro-fluidic card 20 may comprise one or more vents. The vent 26 may be common to all the fluidic circuits. It is also possible to make provision for one separate vent for each fluidic circuit. Each vent may consist of a simple aperture leading to the exterior. Non-limitingly, the vent 26 may also be connected to a source of negative pressure, allowing the filling of each fluidic circuit 21 to be controlled. This source of negative pressure may consist of a syringe 5 or any other pumping solution.

In the location of each detection chamber 23, the card is made from a transparent material. By the term "transparent", what is meant is that the employed material is at least partially transparent to visible light, so as to let at least 80% of this light pass. It thus must be understood that it will be sufficiently transparent for it to be possible to see the interior of the chamber 23.

The entire card 20 may be made from a transparent or semi-transparent material such as polymethyl methacrylate (PMMA), COC or an equivalent. The cartridge inserted into the system advantageously has a (notably fluidic) configuration that is always identical, so as to interact with the elements of the system that are necessarily implemented for the analysis. The chosen material will be the least adsorbent possible, to prevent target molecules (haemoglobin) from adhering to the medium.

Figure 6:
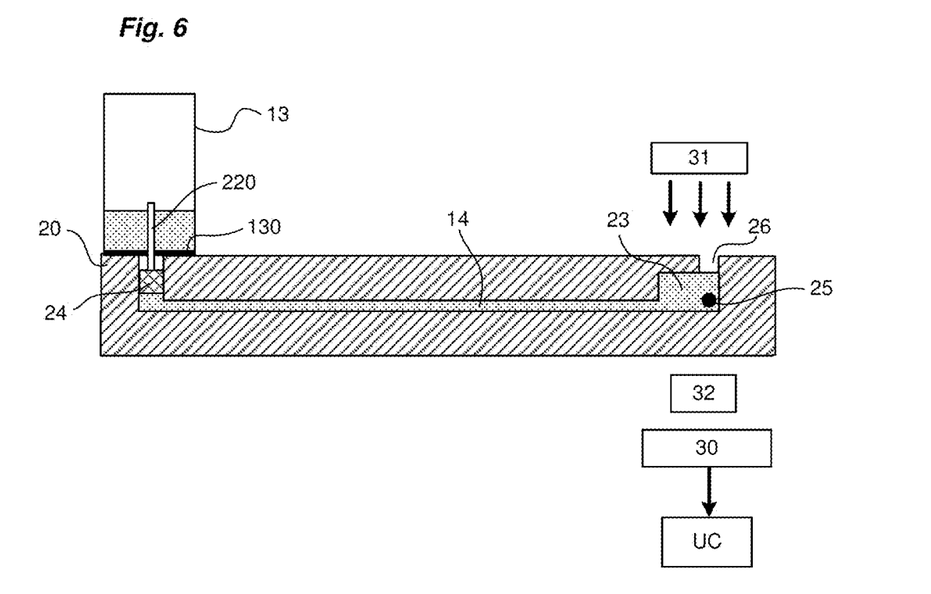
FIG. 6 illustrates the detection concept employed by the system of the invention.

With reference to FIG. 6, the third portion 3 of the system is composed of the optical read-out device allowing the agglutination reaction within each detection chamber 23 to be monitored. The optical read-out may be carried out through a small read-out region of each detection chamber, and need not encompass the entire detection chamber. The optical read-out device may be singular and common to all the detection chambers 23. The optical read-out device comprises at least one sensor 30 and optionally at least one light source 31. The light source 31 may be a light-emitting diode. It is arranged to illuminate the detection chamber of the fluidic circuit 21. The sensor 30 may be a CMOS sensor. It may notably be the sensor present in a smartphone. Optionally, the optical read-out device may comprise a suitable magnifying lens 32 placed between the sensor 30 and the detection chamber 23. When a single device is employed for a plurality of detection chambers, it is possible to provide mechanical actuating means that are controlled to position each detection chamber between the sensor 30 and the light source 31. These means may act on the micro-fluidic card 20 or on the optical read-out device, in order to achieve a relative movement of one with respect to the other. Provision may be made for a movement sequence, in order to scan all the detection chambers of the system. If the sensor 30 is integrated into a smartphone, the light source 31 may be optional.

It will be noted that results may be obtained by employing a diffraction-based imaging concept that is lensless or otherwise employs a lens (a smartphone will already incorporate a lens). Advantageously, the read-out region of the chamber and the sensor are positioned in a defocused manner so as to obtain more contrasted diffraction images of the targets, so as to be able to better distinguish the latter.

Figure 7:
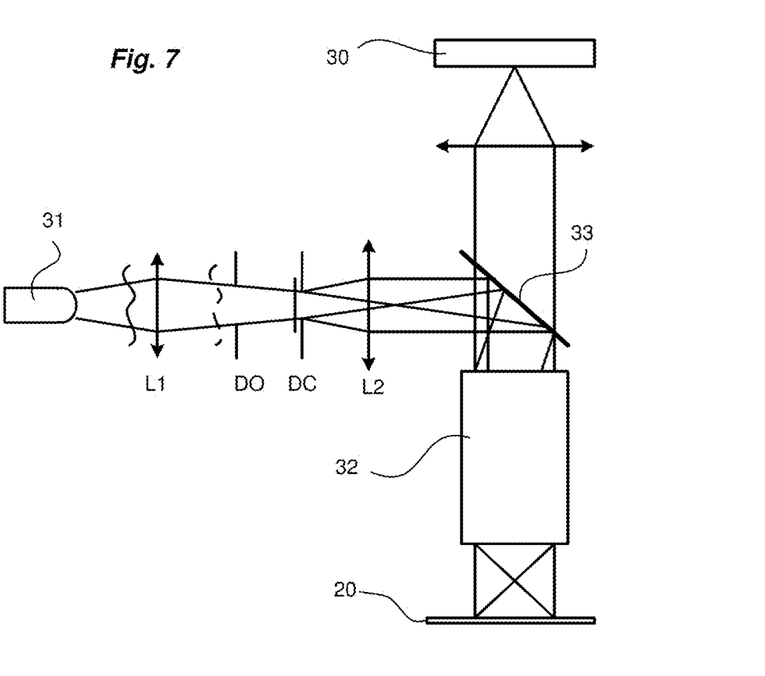
FIG. 7 illustrates a reflection-microscopy concept able to be employed in the system of the invention.

To capture the images, it is notably possible to employ a reflection-microscopy system, as illustrated by FIG. 7. This system comprises a solution for lighting the card 20 bearing the specimen, which solution is composed of the light source 31, of lenses L1, L2, of diaphragms DO, DC and of a reflective plate 33. The magnifying lens 32 is positioned between the plate 33 and the card 20. The sensor 30 is positioned above the plate 33, to capture images of the read-out region of the card 20.

The sensor 30 is intended to capture successive images of the read-out region of the detection chamber 23, thus allowing the progress of the agglutination reaction to be monitored.

The fourth portion 4 of the system is composed of the processing unit UC, which is tasked with processing the images acquired by the sensor 30. This processing unit UC may be that already present in the smartphone the CMOS sensor of which was used to capture the images of the detection chamber. The acquired images are then stored in a memory of the telephone.

The processing unit UC is intended to determine the concentration of the analyte of interest from the images of the detection chamber that were acquired by the sensor 30 then stored in memory.

The images are acquired in defined time intervals over a defined time. During this time, the appearance and notably the texture of the acquired images will change, because of the agglutination of the nano-beads 25 in the presence of the target of interest that it is desired to assay.

Use of a simple indicator (e.g. variation in the standard deviation of the greyscale of a region of interest of the image measured over time) then allows the measurement to be correlated with the amount of target to be assayed.

To this end, the processing unit UC thus comprises a module for determining a texture level of each acquired image and a module for determining a concentration of said analyte depending on the texture level determined for each image.

Example of Experimentally Implemented Processing

Trials have been carried out with a view to detecting human haemoglobin using latex nano-beads grafted with an antibody ("OC Sensor"). To this end, a mini-pig faeces solution was prepared in a commercially available buffer solution and supplemented with a human-haemoglobin range comprised between 0 and 500 ng/mL. This solution was mixed with the reaction buffer solution and the latex beads. Next, a few microlitres of each specimen (simulating sampling) were rapidly placed in the micro-fluidic detection chamber (e.g.: 300 μm thick). This detection chamber was placed facing the CMOS sensor (e.g.: 30 mm$^2$, 1.67 μm CMOS) and illuminated by a light-emitting diode via a pinhole (e.g.: 400 μm fibre-coupled 450 nm LED). For certain trials, a lens was added to the device (e.g.: ×20 objective+×0.3 tube lens, leading to a ×6 magnification). The progress of the agglutination was monitored by acquiring images at regular time intervals (for example: every 5 minutes). A region of interest (ROI) was then defined within the series of images and a relevant indicator of the greyscale of the image (for example: standard deviation or kurtosis) was then chosen in order to allow the images of the selected region of interest to be compared with one another. This indicator was a direct reflection of the variation in the agglutination as a function of time.

Figure 8A:
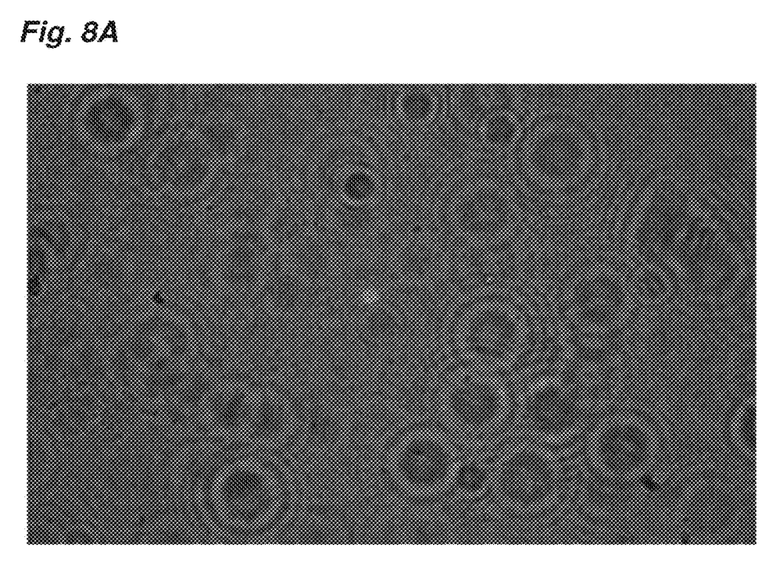
FIGS. 8A and 8B show two images acquired by the sensor of the system of the invention, at t=0 s and t=60 minutes, respectively.
Figure 8B:
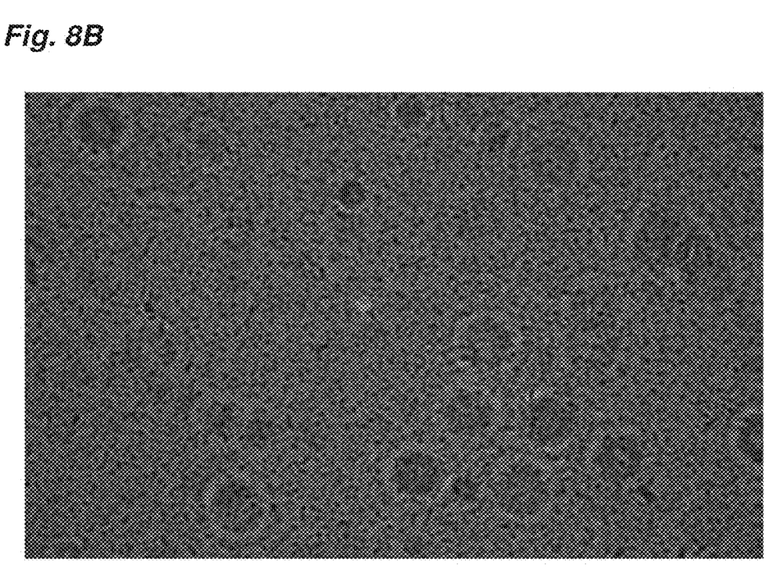
Figure 9A:
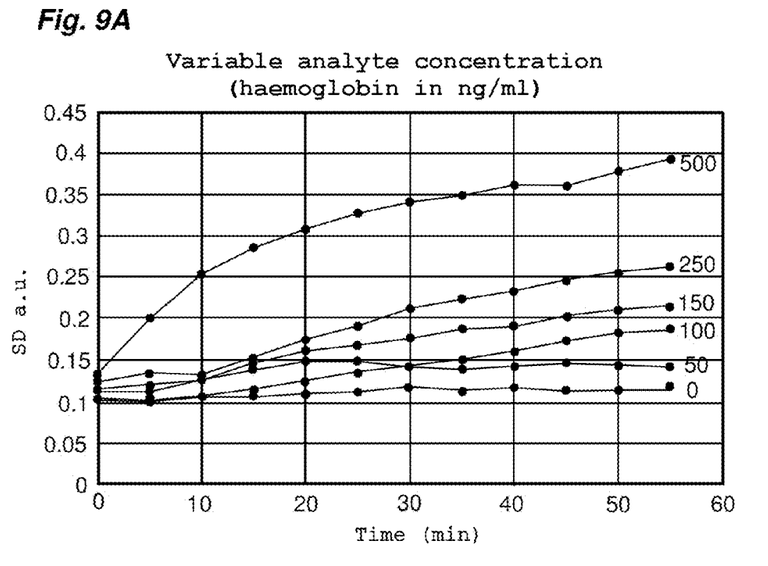
FIGS. 9A and 9B show a graph of the variation in standard deviation as a function of time for various concentrations of haemoglobin and a graph of the variation in normalized standard deviation as a function of concentration of haemoglobin, at t=40 minutes, respectively.
Figure 9B:
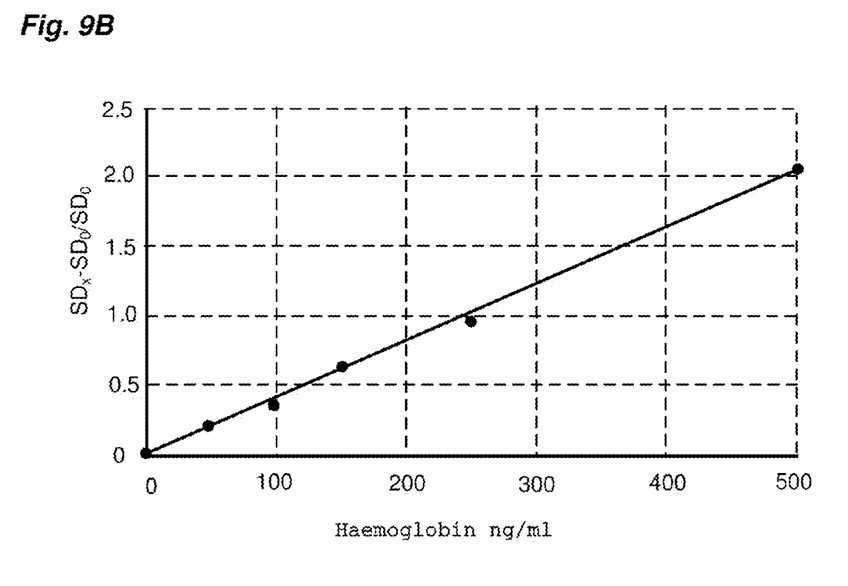

Images obtained using a defocused imaging concept employing a lens showed a change in texture over time that was characteristic of the agglutination reaction that was in the process of taking place. FIGS. 8A and 8B thus show the images obtained at the end of 0 min and 60 min of agglutination reaction with a mini-pig faeces solution. The graph of FIG. 9A shows the variation in the value of the standard deviation (SD) of the greyscale of the region of interest as a function of time. This first texture indicator was enough to quantify the reaction. The graph of FIG. 9B illustrates the value of the indicator $SD_x$ (standard deviation) normalized with respect to $SD_0$ at the end of 40 minutes of reaction as a function of haemoglobin concentration: a linear relationship is visible.

It will be understood from the above that the solution of the invention is particularly advantageous:
  the complete system includes the means for preparing the sample, the detection medium and the read-out and processing device, in a particularly compact architecture, making it easily transportable in the field;
  the system is easy to employ because it uses particularly simple and effective mechanical, electronic and software means;
  the system is effective because it allows a haemoglobin concentration to be determined via simple image processing; it therefore does not require bulky and expensive hardware to be used.

The invention claimed is:

1. A system for detecting an analyte present in a liquid specimen, comprising:

a medium equipped with a fluidic circuit, said fluidic circuit comprising at least one injection channel and a detection chamber into which said injection channel opens, said detection chamber having a non-zero volume enclosing polymeric beads covered with a reagent suitable for said analyte to be detected, a preparing device for preparing the liquid specimen to be analyzed, said medium being fitted on said preparing device, said preparing device comprising a coring implement for coring a sample of material and a dissolving or re-suspending implement for dissolving or re-suspending each core produced by said coring implement, said injection channel of the fluidic circuit being connected to said dissolving or re-suspending implement, an optical read-out device, comprising an image sensor arranged to acquire an image of at least one region of the detection chamber, and a processing unit configured to process the image acquired by the image sensor, comprising a module for determining a texture level of each acquired image and a module for determining a concentration of said analyte depending on the texture level determined for each image, said texture level depending on an agglutination level of the polymeric beads in the detection chamber in the presence of the analyte.

2. The system according to claim 1, wherein the image sensor and the at least one region of the detection chamber are positioned in a defocused manner.

3. The system according to claim 1, wherein the optical read-out device comprises a source of light radiation arranged to emit light radiation through the detection chamber, said image sensor being positioned on the other side of said source with respect to the at least one region of the detection chamber.

4. The system according to claim 1, wherein the medium consists of a micro-fluidic card made from a transparent or semi-transparent material.

5. The system according to claim 4, wherein the dissolving or re-suspending implement comprises one or more cuvettes each intended to receive a dissolving or re-suspending liquid.

6. The system according to claim 5, wherein the preparing device comprises a body and in that the coring implement comprises one or more die-cutters that are movable with respect to the body, each die-cutter interacting translationally with said body in a main direction, between at least one rest state in which the die-cutter is plumb with a deposition surface intended to receive said sample of material and an actuated state in which the die-cutter is located inside a respective cuvette among the one or more cuvettes of the dissolution or re-suspension implement.

7. The system according to claim 6, wherein each cuvette comprises an aperture and at least one perforable film covers the aperture of each cuvette.

8. The system according to claim 1, wherein the fluidic circuit comprises a region for filtering particles present in the liquid specimen.

9. The system according to claim 1, wherein the optical read-out device and the processing unit are grouped together in one and a same device of smartphone type.

* * * * *